United States Patent [19]

Fukui et al.

[11] 4,301,301
[45] Nov. 17, 1981

[54] METHOD FOR PRODUCING TRIPHENYLPHOSPHINE

[75] Inventors: Kiyoshi Fukui; Noboru Kakeya, both of Ichihara, Japan

[73] Assignee: UBE Industries, Ltd., Chiba, Japan

[21] Appl. No.: 145,327

[22] Filed: Apr. 30, 1980

[30] Foreign Application Priority Data

May 11, 1979 [JP] Japan ................... 54-57009

[51] Int. Cl.³ ............................... C07F 9/50
[52] U.S. Cl. ............................................ 568/17
[58] Field of Search ................................ 568/17

[56] References Cited

U.S. PATENT DOCUMENTS 3,060,241 10/1962 Rauhut et al. ................. 568/17
3,223,737 12/1965 Groenweghe ................. 568/17
3,271,460 9/1966 Garner ............................ 568/17
3,361,830 1/1968 van Ghemen et al. ......... 568/17
3,481,988 12/1969 Wünsch et al. ................ 568/17
3,751,481 8/1973 Weinberg ....................... 568/17
4,008,282 2/1977 Townsend et al. ............. 568/17

FOREIGN PATENT DOCUMENTS 1221220 7/1966 Fed. Rep. of Germany ........ 568/17
53-34725 of 1978 Japan .

Primary Examiner—Helen M. S. Sneed
Attorney, Agent, or Firm—Burgess, Ryan and Wayne

[57] ABSTRACT

Triphenylphosphine is produced in a high degree of yield by bringing pressurized hydrogen into contact with a triphenylphosphine dihalide dissolved in a solvent consisting of at least one member selected from monochlorobenzene and dichlorobenzenes.

8 Claims, No Drawings

METHOD FOR PRODUCING TRIPHENYLPHOSPHINE

FIELD OF THE INVENTION

The present invention relates to a method for producing triphenylphosphine from a triphenylphosphine dihalide. More particularly, the present invention relates to an improved method for producing triphenylphosphine from triphenylphosphine dihalide, under a moderate pressure, without producing undesirable by-products.

BACKGROUND OF THE INVENTION

It is known that triphenylphosphine, which is a product of the method of the present invention, is very useful in the synthetic organic chemical industry. For example, triphenylphosphine is used for producing olefines. Also, triphenylphosphine is useful for the synthesis of various useful organic compounds, for example, vitamin A and D. Furthermore, triphenylphosphine is useful for preparing heterocyclic nitrogen compounds by the deoxygenation of nitro and nitroso compounds.

When triphenylphosphine is used for the production of the above-mentioned compounds, the triphenylphosphine per se is converted to triphenylphosphine oxide, which is useless in the chemical industry. No economical method for regenerating triphenylphosphine from triphenylphosphine oxide has been known. However, it is known that triphenylphosphine oxide can be easily converted to a triphenylphosphine dihalide by treating it with a halogenating agent, for example, phosgene, oxalyl halides, thionyl halides and phosphorus pentahalides. Also, triphenylphosphine oxide can be converted to triphenylphosphine dichloride by treating it with chlorine and carbon monoxide in a solvent. This method is disclosed in Japanese Patent Application Laying-open (Kokai) No. 53-142999/1978.

As stated above, the use of triphenylphosphine for various organic chemical processes, results in the production of triphenylphosphine oxide as a by-product, and the triphenylphosphine oxide can be easily converted to a triphenylphosphine dihalide. Therefore, if an economical method for converting the triphenylphosphine dihalide to triphenylphosphine, were provided, the economical method would be remarkably valuable for developing the use of triphenylphosphine.

Also, it is knwon that triphenylphosphine is produced by reacting triphenylphosphine oxide with a silicon tetrahalide and pressurized hydrogen in a solvent, in the presence of sulphur or selenium, under an elevated pressure. This method is disclosed in British Pat. No. 1450830. Further, it is known from Japanese Patent Application Laying-open (Kokai) No. 53-34725/1978 that triphenylphosphine can be produced by reacting triphenylphosphine dihalide with pressurized hydrogen in an aromatic hydrocarbon solvent, for instance, toluene.

However, the above-mentioned former method for producing triphenylphosphine directly from triphenylphosphine oxide, is disadvantageous not only in that it is necessary to use silicon tetrahalide, sulphur and selenium, but also, in that a large amount of a by-product is produced from silicon tetrahalide, and a long time is necessary to complete the conversion. Accordingly, it is difficult to industrially utilize the above-mentioned method. Also, the above-mentioned latter method for producing triphenylphosphine from triphenylphosphine dihalide is disadvantageous in that the stoichiometrical conversion of triphenylphosphine dihalide to triphenylphosphine with a high degree of yield thereof can be effected only under an extremely high pressure of about 100 kg/cm². Also, this method causes corrosive hydrogen halide to be generated during the reaction and, therefore, it is necessary that the reaction be carried out in a glass-coated reactor. Accordingly, it is difficult to utilize the above-mentioned method on an industrial scale.

Under the above-mentioned circumstances, it is strongly desired in the chemical industry to provide an economical method for producing triphenylphosphine under a remarkably lower pressure than 100 kg/cm²G.

On the other hand, it is known from, for example, A. Maercker, "Organic Reactions", Vol. 14, 388 (1967) that halogenated hydrocarbons react with triphenylphosphine to form a phosphonium salt thereof. Therefore, it has seemed to most persons skilled in the art that halogenated hydrocarbon, for example, monochlorobenzene and dichlorobenzens, cannot be used as a solvent for the production of triphenylphosphine.

DISCLOSURE OF THE INVENTION

An object of the present invention is to provide a method for producing triphenylphosphine with a high [degree of] yield thereof.

Another object of the present invention is to provide a method for producing triphenylphosphine under a remarkably lower pressure than 100 kg/cm²G.

The above-mentioned objects can be attained by the method of the present invention, which comprises reacting a triphenylphosphine dihalide with pressurized hydrogen, in a solvent consisting of at least one member selected from the group consisting of monochlorobenzene and dichlorobenzenes.

The method of the present invention is based on the discovery that the production of triphenylphosphine in a solvent consisting of at least one member selected from monochlorobenzene and dichlorobenzenes, does not result in production of a by-product consisting of phosphonium salt of the solvent compound, and can be effected under a relatively low pressure of, for example, about 10 kg/cm².

DETAILED DESCRIPTION OF THE INVENTION

In the method of the present invention, triphenylphosphine is produced from a triphenylphosphine dihalide. The triphenylphosphine dihalide can be produced from triphenylphosphine oxide, which is a by-product of various organic chemical reactions in which triphenylphosphine is used. That is, the method of the present invention makes it possible to industrially utilize triphenylphosphine.

When the reaction of triphenylphosphine oxide with chlorine and carbon monoxide is carried out in a solvent consisting of at least one member selected from monochlorobenzene and dichlorobenzenes, the resultant reaction mixture can be utilized for the production of triphenylphosphine without separating the resultant triphenylphosphine dichloride from the solvent. This is because the solvent used in the production of triphenylphosphine dichloride can be continuously used for the production of triphenylphosphine. This type of process for producing triphenylphosphine from triphenylphosphine oxide is advantageous in that an isolating operation for an intermediate product, triphenylphosphine dichloride, which rapidly absorbes moisture from the atmosphere and is easily hydrolyzed by the absorbed moisture, can be omitted.

Additionally, it should be noted that non-halogenated hydrocarbons, for example, toluene, are useless as a solvent for the process of producing triphenylphosphine from triphenylphosphine oxide. This is because the non-halogenated hydrocarbons are chlorinated during the conversion of triphenylphosphine oxide into triphenylphosphine dichloride.

The triphenylphosphine dihalide usable for the method of the present invention is preferably selected from the group consisting of triphenylphosphine dichloride and triphenylphosphine dibromide. As stated above, it is preferable that the triphenylphosphine dihalide be produced in a solvent consisting of at least one member selected from monochlorobenzene and dichlorobenzenes, and the resultant solution of the triphenylphosphine dihalide be subjected to the process of converting the triphenylphosphine dihalide to triphenylphosphine, without isolating the triphenylphosphine dihalide from the solution. This is because the triphenylphosphine dihalide is very hygroscopic and easily hydrolyzed.

The solvent may consist of monochlorobenzene or a dichlorobenzene alone, or a mixture of two or more of the above-mentioned chlorobenzenes. In order to avoid the hydrolysis of triphenylphosphine dihalides, it is preferable that the solvent be satisfactorily dried before being used. The solvent is preferably used in an amount of from 5 to 50 times more preferably, from 7 to 20 times, the weight of the triphenylphosphine dihalide.

The reaction of the triphenylphosphine dihalide with hydrogen in the solvent is carried out by blowing the hydrogen gas into the solution of the triphenylphosphine dihalide under an elevated pressure, preferably, under a partial pressure of hydrogen of from 1.5 to 50 $kg/cm^2G$, more preferably, from 2 to 30 $kg/cm^2G$, most preferably, from 2 to 10 $kg/cm^2G$. When the partial pressure of the hydrogen gas is lower than 1.5 $kg/cm^2G$, usually, the conversion of the triphenylphosphine dihalide is not satisfactorily effected. For example, when the hydrogen gas is blown into the solution of triphenylphosphine dihalide under atmospheric pressure, the conversion of triphenylphosphine dihalide is effected at such a very low conversion rate that the conversion cannot be utilized for industrial purposes. Also, even if the partial pressure of the hydrogen gas is increased to more than 50 $kg/cm^2G$, such increase not only has no effect in accelerating the conversion of the triphenylphosphine dihalide, but also, causes an undesirable necessity of carrying out the conversion of triphenylphosphine dihalide in a high pressure reaction equipment. This necessity results in the production of triphenylphosphine being expensive.

The reaction of the triphenylphosphine dihalide with hydrogen is preferably carried out in the absence of molecular oxygen-containing gas, for instance, air. Therefore, it is preferable that air in the reaction vessel be replaced by hydrogen or an inert gas before charging triphenylphosphine dihalide and the solvent into the vessel. Otherwise, after the triphenylphosphine dihalide and the solvent are placed in the reaction vessel, air in the reaction vessel is discharged and, then, hydrogen gas is flowed into the reaction vessel, in such an amount that the partial pressure of the hydrogen gas reaches a desired value.

Thereafter, the reaction mixture is heated to a predetermined reaction temperature. Usually, the reaction is carried out at a temperature of from 100° to a 250° C., preferably, from 150° to 220° C. The reaction time is variable depending on the reaction temperature and pressure. For example, the reaction at a temperature of 200° C. can be completed within one hour, and the reaction at a temperature of 180° C. can be completed within about two hours.

After the reaction is completed, the resultant reaction mixture contains, in addition to the desired product, namely, triphenylphosphine, a by-product consisting of hydrogen halide; the solvent; and, the remaining unreacted triphenylphosphine dihalide.

The resultant triphenylphosphine can be isolated from the reaction mixture by any conventional isolating method. For example, the reaction mixture can be treated with an alkaline aqueous solution containing a neutralizing agent consisting of at least one member selected from carbonates, hydrogen bicarbonates and hydroxides of alkali metals and alkaline earth metals, so as to allow a solution of the resultant triphenylphosphine in the solvent to be separated from the reaction mixture, and then, the solution of triphenylphosphine is subjected to distillation.

According to the method of the present invention, it is possible to produce triphenylphosphine under a lower partial pressure of hydrogen than that in conventional method, with a high degree of yield thereof, without producing undesirable phosphonium salt, which has been believed to be produced from the chlorinated benzene and the triphenylphosphine.

Also, according to the method of the present invention, the reaction mixture containing a triphenyphosphine dichloride which has been produced by reacting triphenylphosphine oxide with chlorine and carbon monoxide in a solvent consisting of at least one member selected from monochlorobenzene and dichlorobenzenes, can be continuously utilized as a material for the production of triphenylphosphine. That is, the conversion of the triphenylphosphine oxide to triphenylphosphine dichloride and the conversion of triphenylphosphine dichloride to triphenylphosphine can be carried out in the same solvent.

The following specific examples are presented for the purpose of clarifying the method of the present invention. However, it should be understood that these examples are intended only to illustrate the present invention and are not intended to limit the scope of the present invention in any way.

In the examples, the yield of triphenylphosphine was based on the molar amount of triphenylphosphine dihalides used.

EXAMPLES 1 THROUGH 4

In Example 1, 3.36 g (12 millimoles) of triphenylphosphine oxide and 1.54 g (12 millimoles) of oxalyl chloride were dissolved in 50 ml of monochlorobenzene, and the solution was left standing until the evolution of carbon monoxide and carbon dioxide from the solution was completed. A solution of 12 millimoles of triphenylphosphine dichloride in 50 ml of monochlorobenzene was obtained. That is, the conversion of triphenylphosphine oxide to triphenylphosphine dichloride was effected stoichiometrically.

The triphenylphosphine dichloride solution was placed in a glass vessel, the glass vessel was placed in a stainless steel autoclave. After closing the autoclave, air in the autoclave was removed, and hydrogen gas was flowed into the autoclave until the partial pressure of the hydrogen gas reached 20 kg/cm$^2$G. Thereafter, the autoclave was heated at the temperature of 180° C., for two hours, while being shaken, so as to allow the triphenylphosphine dichloride to react with hydrogen.

After the reaction was completed, an aqueous solution of 20% by weight of sodium hydrogen carbonate was added to the reaction mixture, while stirring it, to neutralize the reaction mixture and to separate a solution of the resultant triphenylphoshine in monochlorobenzene from the reaction mixture. The triphenylphosphine solution was dried by using sodium sulfate anhydride and, then, distilled at a temperature, to remove monochlorobenzene. Triphenylphosphine in the form of colorless crystals was obtained in the yield as indicated in Table 1.

In each of Examples 2, 3 and 4, the same procedures as those mentioned in Example 1 were carried out, except that triphenylphosphine dichloride was used in an amount of 10 millimoles, the partial pressure of hydrogen gas in the autoclave was as indicated in Table 1, and the reaction temperature and time were those as indicated in Table 1. The yield of the resultant triphenylphosphine is indicated in Table 1.

EXAMPLE 5

The same procedures as those described in Example 3 were carried out, except that 50 ml of dichlorobenzene were used for the monochlorobenzene. The yield of the resultant triphenylphosphine is indicated in Table 1.

Comparison Example 1

The same procedures as those described in Example 1 were carried out, except that a solution of 12 millimole of triphenylphosphine dichloride in 50 ml of toluene was used. The yield of triphenylphosphine is indicated in Table 1.

TABLE 1

| Example No. | Amount of Triphenyl-phosphine dichloride (m mol) | Solvent | Partial pressure of H$_2$ (kg/cm$^2$G) | Temperature (°C.) | Time (hr) | Yield of triphenylphosphine (%) |
|---|---|---|---|---|---|---|
| Example 1 | 12 | Monochlorobenzene | 20 | 180 | 2 | 98 |
| Example 2 | 10 | Monochlorobenzene | 5 | 180 | 2 | 91 |
| Example 3 | 10 | Monochlorobenzene | 5 | 200 | 1 | 98 |
| Example 4 | 10 | Monochlorobenzene | 3 | 200 | 1 | 100 |
| Example 5 | 10 | Dichlorobenzene | 5 | 200 | 1 | 95 |
| Comparison Example 1 | 12 | Toluene | 20 | 180 | 2 | 73 |

EXAMPLE 6

A solution of 90 millimoles of triphenylphosphine dichloride in 200 ml of monochlorobenzene was prepared by methods similar to those described in Example 1. The solution was placed in an autoclave. Air in the autoclave was removed and hydrogen gas was blown into the autoclave under a pressure of 5 kg/cm$^2$G. The autoclave was heated to a temperature of 160° C., so as to allow the triphenylphosphine dichloride to react with hydrogen. The temperature of the reaction mixture was maintained at 160° C., and the hydrogen gas was flowed through the autoclave at a flow rate of 450 ml/min, while maintaining the pressure of the reaction mixture at 10 kg/cm$^2$G, while stirring the reaction mixture and discharging exhaust gas from the autoclave. The reaction was continued for eight hours until no hydrogen chloride was found in the exhaust gas.

After the reaction was completed, the reaction mixture was treated in the same manner as described in Example 1 to isolate the resultant triphenylphosphine. The yield of the triphenylphosphine was 90%.

EXAMPLE 7

A solution of 2.78 g (10.0 millimoles) of triphenylphosphine oxide and 0.92 g (13.0 millimoles) of chlorine in 50 ml of monochlorobenzene was placed in a glass vessel and the glass vessel was placed in an autoclave. A carbon monoxide gas was blown into the autoclave under a pressure of 5 kg/cm$^2$G. The solution was heated at a temperature of 160° C., for one hour, while shaking the autoclave. A reaction mixture containing triphenylphosphine dichloride dissolved in monochlorobenzene was obtained.

After the above-mentioned reaction was completed, the resultant reaction mixture was cooled to a room temperature, and gas in the autoclave was removed. Next, hydrogen gas was blown into the autoclave so that the partial pressure of hydrogen in the autoclave reached 3 kg/cm$^2$G. The reaction mixture was heated at a temperature of 200° C. for two hours.

After the reaction was completed, the reaction mixture was treated in the same manner as described in Example 1, to isolate the resultant triphenylphosphine from the reaction mixture. The yield of the triphenylphosphine was 94%.

We claim:

1. A method for producing triphenylphosphine comprising reacting, a triphenylphosphine dihalide with pressurized hydrogen in a solvent consisting of at least one member selected from the group consisting of monochlorobenzene and dichlorobenzenes.

2. A method as claimed in claim 1, wherein said triphenylphosphine dihalide is selected from the group consisitng of triphenylphosphine dichloride and triphenylphosphine dibromide.

3. A method as claimed in claim 1, wherein said solvent is used in an amount of from 5 to 50 times the weight of said triphenylphosphine dihalide.

4. A method as claimed in claim 1, wherein the partial pressure of hydrogen is in a range of from 1.5 to 50 kg/cm²G.

5. A method as claimed in claim 4, wherein the partial pressure of hydrogen is in a range of from 2 to 30 kg/cm²G.

6. A method as claimed in claim 5, wherein the partial pressure of hydrogen is in a range of from 2 to 10 kg/cm²G.

7. A method as claimed in claim 1, wherein said reaction is carried out at a temperature of from 100° to 250° C.

8. A method as claimed in claim 1, wherein the resultant triphenylphosphine is isolated by treating the reaction mixture with an alkaline aqueous solution to separate a solution of the resultant triphenylphosphine in said solvent from said reaction mixture and, then, by subjecting said triphenylphosphine solution to distillation.

* * * * *

UNITED STATES PATENT AND TRADEMARK OFFICE
CERTIFICATE OF CORRECTION

PATENT NO. : 4,301,301
DATED : November 17, 1981
INVENTOR(S) : Kiyoshi Fukui et al It is certified that error appears in the above—identified patent and that said Letters Patent is hereby corrected as shown below:

Column 1, line 48 : "knwon" should be --known--

Column 2, line 5 : "$100kg/cm^2$" should be --$100kg/cm^2G$--

Signed and Sealed this

Tenth Day of May 1983

[SEAL]

Attest:

GERALD J. MOSSINGHOFF

Attesting Officer     Commissioner of Patents and Trademarks